(12) United States Patent
von Oepen

(10) Patent No.: US 7,771,459 B2
(45) Date of Patent: Aug. 10, 2010

(54) FASTENER HAVING TORQUE OPTIMIZED HEAD

(75) Inventor: Randolf von Oepen, Los Altos Hills, CA (US)

(73) Assignee: Degima GmbH, Pinneberg (DE)

( * ) Notice: Subject to any disclaimer, the term of this patent is extended or adjusted under 35 U.S.C. 154(b) by 0 days.

(21) Appl. No.: 11/145,692

(22) Filed: Jun. 6, 2005

(65) Prior Publication Data

US 2006/0293677 A1    Dec. 28, 2006

Related U.S. Application Data

(60) Provisional application No. 60/577,639, filed on Jun. 7, 2004.

(51) Int. Cl.
A61B 17/86 (2006.01)
A61B 17/58 (2006.01)

(52) U.S. Cl. .................. 606/301; 606/305; 606/104

(58) Field of Classification Search ............. 606/72–73; 411/402–404
See application file for complete search history.

(56) References Cited

U.S. PATENT DOCUMENTS

| | | | | |
|---|---|---|---|---|
| 1,909,476 A | * | 5/1933 | Trotter | 411/386 |
| 2,096,937 A | * | 10/1937 | McManus | 411/418 |
| 2,156,350 A | * | 5/1939 | Olson | 411/420 |
| 2,160,706 A | * | 5/1939 | Olson | 411/420 |
| 2,268,515 A | * | 12/1941 | Olson | 81/460 |
| 2,302,675 A | * | 11/1942 | Cherry | 411/421 |
| 2,397,216 A | * | 3/1946 | Stellin | 411/404 |
| 2,494,229 A | * | 1/1950 | Collison | 606/73 |
| 2,800,829 A | * | 7/1957 | West | 411/404 |
| 3,695,321 A | * | 10/1972 | Garehime, Jr. | 81/448 |
| 3,872,904 A | * | 3/1975 | Barlow | 81/460 |
| 4,202,244 A | * | 5/1980 | Gutshall | 411/404 |
| 5,019,080 A | * | 5/1991 | Hemer | 606/73 |
| 5,353,667 A | * | 10/1994 | Wilner | 81/436 |
| 5,435,680 A | * | 7/1995 | Schuster | 411/404 |
| 5,470,334 A | * | 11/1995 | Ross et al. | 606/72 |
| 5,598,753 A | * | 2/1997 | Lee | 81/460 |
| 5,957,645 A | * | 9/1999 | Stacy | 411/404 |

(Continued)

OTHER PUBLICATIONS

João F. Mano et al., *Bioinert, biodegradable and injectable polymeric matrix composites for hard tissue replacement: state of the art and recent developments*, Composites Science and Technology 64 (2004) 789-817.

(Continued)

*Primary Examiner*—Nicholas D Lucchesi
*Assistant Examiner*—Mary Hoffman
(74) *Attorney, Agent, or Firm*—Workman Nydegger

(57) ABSTRACT

Disclosed is a medical fastener that can be mounted to a bone of a patient. The medical fastener can include a head portion comprising a recess having a first portion, a second tapered portion extending from the first portion, and a third cylindrical portion extending from the second tapered portion. A threaded body portion can extend from the head portion. The first portion and the second portion can have a Torx geometry or star-shaped configuration. Also disclosed is a driver usable to mount the medical fastener to the bone. The driver can include a tip that is complementary to the recess and an end that enables the driver to mount to a drill or other device that can rotate the driver.

19 Claims, 1 Drawing Sheet

U.S. PATENT DOCUMENTS

| | | | | |
|---|---|---|---|---|
| 6,128,983 A * | 10/2000 | Arnn | ................ | 81/460 |
| 6,149,653 A * | 11/2000 | Deslauriers | ................ | 606/72 |
| 6,341,546 B1 * | 1/2002 | Totsu | ................ | 81/460 |
| 6,398,785 B2 * | 6/2002 | Carchidi et al. | ................ | 606/73 |
| 6,951,158 B1 * | 10/2005 | Edland | ................ | 81/460 |
| 2003/0125749 A1 * | 7/2003 | Yuan et al. | ................ | 606/104 |

OTHER PUBLICATIONS

Christiane König et al., *Autosterilization of biodegradable implants by injection molding process*, printed from the website: http://www3.interscience.wiley.com/cgi-bin/abstract/44214/ABSTRACT on May 21, 2005, (2 pages).

C. Mauli Agrawal et al., *Biodegradable polymeric scaffolds for musculoskeletal tissue engineering*, Copyright 2001 John Wiley & Sons, Inc. (10 pages).

User's Manual for Textron Fastening Systems Torx Plus Drive System printed from the website: http://www.textronfasteningsystems.com/pdfs/TP_tech/TPbrochure.pdf on May 21, 2005, (15 pages).

* cited by examiner

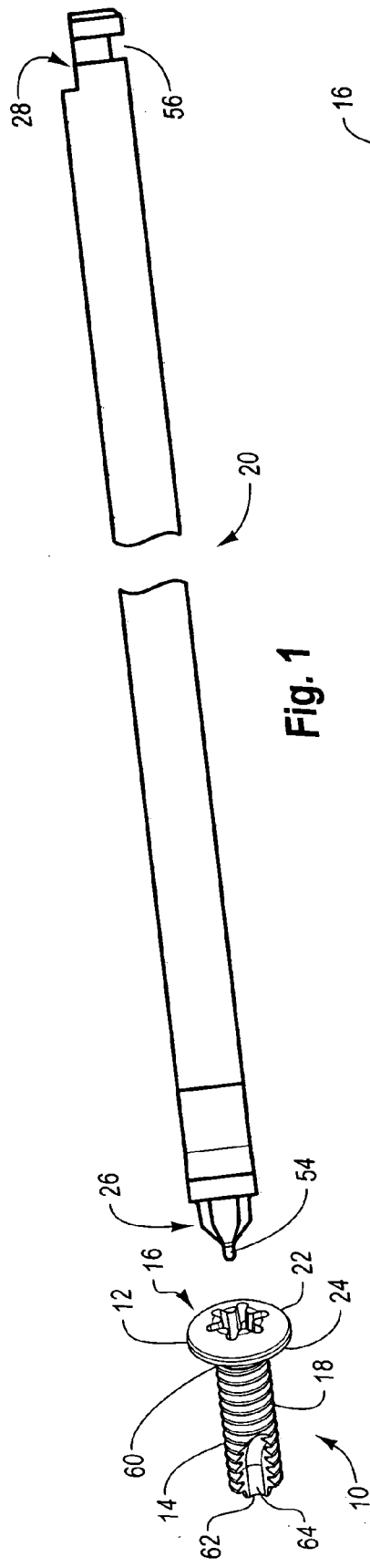
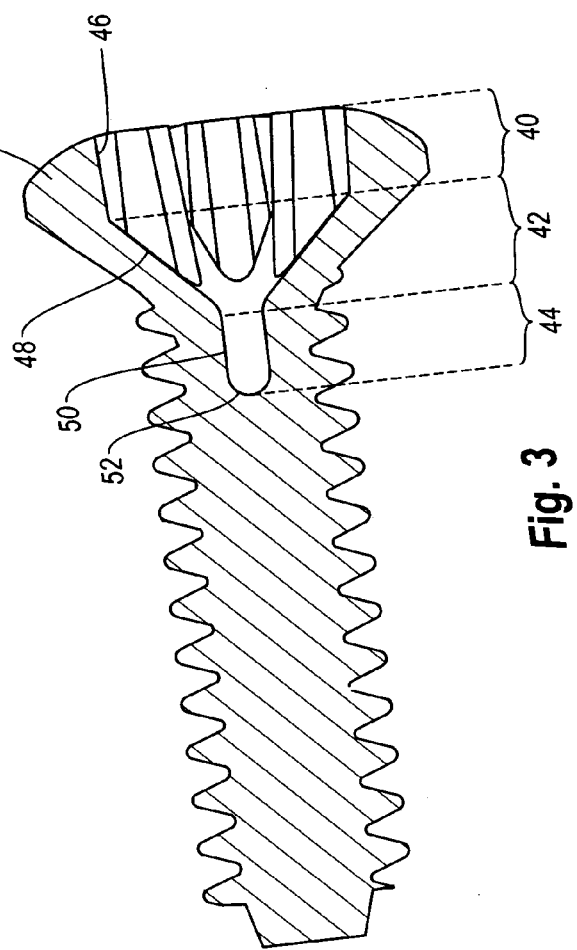
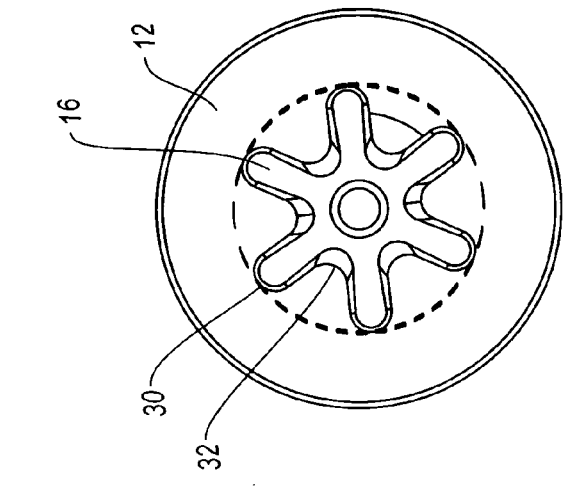

FASTENER HAVING TORQUE OPTIMIZED HEAD

CROSS-REFERENCE TO RELATED APPLICATIONS

This patent application claims the benefit of U.S. Provisional Patent Application No. 60/577,639, filed Jun. 7, 2004, and entitled "Polymeric Screw with Optimized Head for Torque Transmission and a Clearance at the Distal End", the disclosure of which is incorporated herein.

BACKGROUND OF THE INVENTION

1. The Field of the Invention

This application relates generally to fasteners. More specifically, the present invention relates to a medical fastener having a head optimized to transmit torque and to limit the possibility of damage to the head or threads during use.

2. The Relevant Technology

Conventional fasteners, such as screws, are used in a wide range of applications, ranging from wood working to medical procedures. Different screw head geometries have been developed to transmit torque from a driver to the screw head and the screw shaft. For metallic screws the most popular types of head are slotted heads or cruciform heads. A blade-type driver is typically used with a slotted head screw, while a cruciform-type driver is used with a cruciform head.

Although these are the common types of screw head, they suffer from significant problems, especially when used for medical procedures. For instance, during use of a slotted head screw it is typical for the blade-type driver to slide out of the slot resulting in damage to the materials surrounding the screw. This can be detrimental to the surrounding bone or tissue into which the screw is placed. With respect to the cruciform-type screws, the forces applied to the screw by way of the cruciform-type driver can result in the tip of the driver being forced out of engagement with the screw. In addition, the limits of torque transfer associated with the cruciform-type screw can prevent the screw from being fully seated during use. In either case, this can be detrimental to a beneficial outcome to bone growth and rehabilitation of the patient.

Due to the high mechanical properties of metals, metallic screws can include a slot head or cruciform head to enable the transfer of the high torques. Unfortunately, for polymeric screws it is difficult to apply the desired torque to secure the screw, because the head of the screw will typically be stripped under high torques. This is especially true for biodegradable screws for medical applications. It is often impossible to apply adequate axial force to a biodegradable screw when attempting to fixate small bone fragments or thin bone structure. A simple slot is not optimal since the driver blade can slide out of the screw head and damage the surrounding tissue. A recessed head offers more surface area due to it conical shape, but since plastics and in specific biodegradable polymers have a low young modulus the driver blade can over-wind and destroy the screw head.

In addition to the above, problems can occur with current screws that prevent the screw from being completely driven into the bone or structure. To secure a good fixation of the screw in a bone the hole in the bone is usually tapped to create a threaded hole. There is a tendency that blood and scale of bone will be in the threaded hole. If a screw is screwed into the threaded hole the scale of bone, particles and blood will be pressed between the screw and the threads formed in the threaded hole and will increase the frictional contact between the screw and the threads. Depending on the amount of material remaining in the thread hole the generated friction can be so high that it is not possible to mount the screw within the threaded hole without destroying the screw head or the threads.

BRIEF SUMMARY OF THE INVENTION

The present invention generally relates to fasteners, such as, but not limited to, polymer and/or biodegradable screws, that allow a secure transmission of torque into the screw without a risk of damaging the fastener head. The present invention also relates to fasteners that can be securely mounted to a driver without the use of magnetic attraction, as is commonly used for metallic screws. In addition, the present invention relates to a fastener that can guide particulates or material dislodged from the bone or structure into which the fastener is driven to limit binding of the fastener during positioning of the fastener within the bone or structure.

In one configuration, a medical fastener includes a head portion having a recess with a first portion, a second tapered portion extending from the first portion, and a third cylindrical portion extending from the second tapered portion. The first portion and the second tapered portion having a generally star-shaped cross-section, such as can receive a Torx-type driver. Extending from the head portion is a threaded body portion that includes a channel to collect or guide particles, blood, etc, during driving the medical fastener into the bone of a patient. This channel can curve as it extends from one end of the threaded body portion to the other.

In another configuration, a system for mounting a medical fastener to a bone of a patient can include a driver. The driver can mount to a drill or other device that rotates the driver. Disposed at one end of the driver is a tip that can have a first cylindrical portion and a second tapered portion. The first cylindrical portion and the second tapered portion having a Torx geometry that is complementary to a recess to a medical fastener. Extending from the second portion is a pin that mounts to the recess through an interference fit or frictional engagement. By so doing, the medical fasteners mounts to the driver, reducing unwanted handling and maintaining sterility of the medical fastener.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 illustrates a perspective view of a fastener and driver according to the present invention;

FIG. 2 illustrates a top view of a fastener of the present invention; and

FIG. 3 illustrates a cross-sectional side view of the fastener of the present invention.

DETAILED DESCRIPTION OF THE EMBODIMENTS

The present invention generally relates to fasteners, such as a polymer screw and/or biodegradable screws, which allow a secure transmission of torque into the fastener without a risk of damaging the fastener's head. The present invention also relates to fasteners that can be securely mounted to a driver to maintain sterility of the fastener. In addition, the present invention relates to a fastener that can guide particulates or material dislodged from the bone or structure into which the fastener is driven to limit binding of the fastener during positioning of the fastener within the bone or structure.

Turning to FIG. 1, illustrated is a fastener 10 and a driver 20 according to one aspect of the present invention. The fastener 10, such as a screw, can be used during a medical procedure to aid with positioning bone or fixing other medical devices to patient bone. The driver 20 can be used either alone or in combination with an electric drill or other device for rotating the driver 20 to mount the fastener 10 into the bone. Although the description herein will be directed generally to use of the fastener 10 and driver 20 for medical procedures, it will be understood by those skilled in the art that the features of the fastener 10 and the driver 20 may apply to other situations. Consequently, the presently described fastener 10 and driver 20 may be used in other situations outside of the medical arts.

With continued reference to FIG. 1, the illustrated fastener 10 can include a fastener head or head portion 12 and a body portion 14 extending from the head portion 12. The head portion 12 can include a recess 16 to receive a driver 20 usable to mount the fastener 10 within the bone of a patient, while a thread 18, such as a raised helical rib, winds around the body portion 14 and can engage with a patient's bone as the driver 20 rotates the fastener 10. Since the head portion 12 has a diameter greater than the body portion 14, the head portion 12 prevents excessive mounting of the fastener 10 to the bone of a patient, i.e., the head portion 12 prevents the fastener 10 from being driven too deeply into the bone.

As shown herein, the head portion 12 has a curved portion 22 and a generally tapered portion 24. The tapered portion 24 allows the fastener 10 to be countersunk into the bone of the patient, when appropriate. It will be understood, however, that each of the curved portion 22 and the tapered portion 24 can have other configurations. For example either or both of the curved portion 22 and the tapered portion 24 can be planar. Similarly, although the head portion 12 is illustrated as having a generally circular peripheral edge, one skilled in the art can appreciate that the peripheral edge can be polygonal, oval, or any other configuration.

Similarly, while the body portion 14 is illustrated as having a generally uniform cross-section along its length, it will be understood that the body portion 14 can have a tapered configuration or some other configuration so long as the body portion 14 can engage with the patient's bone or other structure within which the fastener 10 is driven. In addition, it will be understood that the head portion 12 and the body portion 14 can have various other configurations that are typically associated with a screw and more generally a threaded fastener or anchor, i.e., a fastener, anchor, or other device that can include one or more threads to aid mount the fastener, anchor, or device to a structure. For instance, the "fastener" of the present invention can include, but is not limited to, screws, bone anchors, suture material which will foreshorten, i.e. bone pins, components of a meniscus repair system, clamps, or other devices that can obtain a benefit from utilizing the features and functions of the present invention.

Turning to FIG. 2, the recess 16 of the head portion 12 has a generally star shaped configuration with a plurality of indentations 30 and extensions 32. The generally star-shaped configuration can be similar to a Torx geometry. In the illustrated configuration, the perimeter of each indentation 30 and extension 32 is generally curved to create a generally smooth transition from one indentation 30 to one extension 32. It can be appreciated that the perimeter of each indentation 30 and extension 32 can be generally planar so that the transition between one indentation 30 and one extension 32 is more abrupt and angular.

The generally star-shaped configuration of the recess 16 extends from a first portion 40 to a second portion 42, as illustrated in FIG. 3. The first portion 40 can include an internal wall 46 that is slightly angularly orientated relative to or parallel to a longitudinal axis of the fastener 10. In either case, the recess 16 can securely receive the driver 20 (FIG. 1) and reduces the possibility that forces applied to the driver 20 (FIG. 1) will cause the driver to be forced from the recess 16. This configuration also maintains desired torque transfer between the driver and the fastener 10. Generally, the first portion 40 can be a cylindrical portion of the recess 16.

As mentioned, the star-shaped configuration of the recess 16 also extends to the second portion 42. The second portion 42 has a generally tapered configuration with a tapered wall 48. With the combination of the first portion 40 and the second portion 42, the available surface area capable of contacting the driver 20 (FIG. 1) is increased as compared with existing Torx or cruciform-type screws and drivers. This increased surface area enables secure transmission of torque between the fastener 10 and the driver 20 (FIG. 1), while reducing the tendency of a driver to be leveraged from the recess 16. For polymeric fasteners and biodegradable fasteners this eliminates many of the problems with current technologies, such as stripping the head of the fastener or otherwise damaging the fastener during mounting to bone or another surface.

Extending from the second portion 42 is a third portion 44. The third portion 44 aids with limiting unwanted handling of the fastener 10 during medical procedures. Generally, fasteners for medical applications have to be sterile and so contamination during the handling of the screw is avoided. To aid with handling, the present invention can include a third portion 44 in the recess 16.

As illustrated in FIG. 3, the third portion 44 has a wall 50 that is generally parallel to the longitudinal axis of the fastener 10. This wall 50 terminates at a generally curved base 52 that can be disposed within a portion of the body portion 14. The third portion 44 is configured to interference or friction fit with a tip 26 of the driver 20 (FIG. 1). For instance, a pin 54 of the tip 26 can engage the third portion 44. With the pin 54 (FIG. 1) being generally tapered and slightly larger in diameter than the interior diameter of the third portion 44, and due to the fastener 10 having a lower young modulus as compared to the metallic driver 20 (FIG. 1), the tip 26 of the driver 20 (FIG. 1) can be pressed into softer material of the head portion 12. By pressing the pin 54 (FIG. 1) of the tip 26 (FIG. 1) into the recess 16, the driver 20 (FIG. 1) and the fastener 10 fit together and the fastener 10 can stick to the driver 20 (FIG. 1) via friction. More generally, the pin 54 (FIG. 1) can interference fit with the third portion 44 of the recess 16. To optimize this friction the surface of the pin 54 and/or the tip 26 (FIG. 1) can be roughened for example by sandblasting or other methods known to those skilled in the art.

Although reference is made to the pin 54 fitting together with the third portion 44 of the recess 16 by way of frictional or interference contact to aid with handling of the fastener, it can be understood, however, that any portion of the tip 26 can frictionally or interference fit with and be pressed into any portion of the softer material of the head portion 12 to aid with handling of the fastener. Therefore, any one or combination of the first portion 40, the second portion 42, and/or the third portion 44 can be used to aid with handling of the fastener and maintain sterility since the tip 26 can frictionally or interference fit with and be pressed into any one or combination of the portions 40, 42, or 44 the fastener.

Returning to FIG. 1, the thread 18 of the body portion 14 extends from a first end 60 toward a second tapered end 62. Interrupting the thread 18 is a channel 64 having an open end at the second tapered end 62. This channel 64 provides clearance at the end of the fastener 10 to collect particles, such as scale of bone, particles and blood, which are within a hole, optionally tapped, receiving the fastener 10. By collecting the scale of bone, particles and blood, the channel 64 eliminates the possibility that scale of bone, particles and blood can press between the fastener 10 and the hole's wall or threads and prevent the fastener or screw from being driven into the hole. Including the channel 64 significantly reduces the frictional contact between the fastener 10 and the hole's wall or threads, thereby making it easier to mount the fastener 10 to the patient's bone.

As illustrated, the channel 64 extends and curves from the tapered second end 62 toward the first end 60 and terminates distal to the first end 60 in a taper. In other configurations, the channel 64 can extend to the first end 60, with or without a taper. The channel 64 curves in a direction opposite to the direction of rotation of the thread 18. Stated another way, the channel 64 curves in the direction opposite to the rotation of the fastener 10 during mounting of the fastener 10 into a patient's bone. In other configurations, the channel 64 can curve in the direction of rotation of the fastener 10 or can optionally have a longitudinal axis parallel to the longitudinal axis of the fastener 10.

To drive the fastener 10 into the bone, the present invention can optionally include the driver 20. The driver 20 is a generally elongated shaft having the tip 26 and a notched end 28. The tip 26 has a configuration generally complementary to the recess 16 of the fastener 10. As such, the tip 26 has a generally star-shaped cross-section with portions complementary to the first portion 40, the second portion 42, and the third portion 44, i.e., a first portion that is optionally cylindrical, a tapered second portion, and the pin 54 generally centered on the tip 26. So long as the tip 26 can drivingly engage with the fastener 10, the tip 26 can have various other configurations known to those skilled in the art.

The notched end 28 enables the driver 20 to mount to an electric drill or other device that can rotate the driver 20. For instance, the driver 20 can act as a drill bit to the electric drill or other device that can rotate the driver 20. With the illustrated configuration, the notch 56 of the notched end 28 can engage with a complementary structure of the electric drill, for example, that mechanically couples the driver 20 to the electric drill. It will be understood that such mechanical coupling can be achieved without the notch 56. For instance, the shaft of the driver 20 can have a hexagonal, square, oval, circular, or generally polygonal configuration that provides the desired surface area for a chuck of an electric drill to mechanically couple the driver 20 to the electric drill. In other configurations, the driver 20 can include a handle (not shown) so that a physician can manually rotate the fastener 10 using the driver 20.

When the fastener 10 of the present invention is to be used within the medical field, the fastener 10 can be fabricated from a medical grade polymer, synthetic material, biocompatible material, or a biodegradable material, such as poly-l-lactic acid (PLLA) that can be absorbed into adjacent bone tissue over time as the repair site heals. Other biodegradable materials suitable for use in the fastener are known to those skilled in the art. In certain circumstances, the fastener 10 can be fabricated from a metal or metal alloy, such as a titanium alloy or stainless steel.

In addition to the above described polymers, provided here below are additional materials that can be used to form the fastener 10. Generally, the polymers can include a wide range of biocompatible materials that can be implanted within a body. Additionally, the polymers can be combined and blended in order to achieve compositions that have the desired properties and characteristics.

In one embodiment, a polymer composition for use in injection molding a biocompatible fastener can include at least one biodegradable polymer. For example, the biodegradable polymer composition can include at least one of poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, or the like. Additionally, these polymers can be used at a wide range of molecular weights, which can range from less than about 25,000 MW to over 1,000,000 MW. More particularly, the molecular weight can vary depending on the type of polymer, initial strength, fastener degradation rate, and the like. Additional information on the tensile strength, tensile modulus, flexural modulus, and elongations at yield and at break of various biocompatible and biodegradable polymers can be found with Engelberg and Kohn; Physico-mechanical Properties of Degradable Polymers Used in Medical Applications: A Comparative Study; *Biomaterials;* 1991; 12:292-304, which is incorporated herein by reference.

In one embodiment, a polymer composition for use in injection molding a biocompatible fastener can include at least one inert polymer. For example, the inert polymer can include at least one of high-density polyethylenes, ultra-high-density polyethylenes, low-density polyethylenes, polypropylenes, polyacrylates, polymethylmethacrylates, polyethylmethacrylates, polysulfones, polyetheretherketones, polytetrafluoroethylenes, polyurethanes, polystyrenes, polystyrene-co-butadienes, epoxies, and the like. Such inert polymers can be used at a wide range of molecular weights in order to impart various mechanical strengths to the polymeric fastener.

In one embodiment, the polymer composition for use in injection molding a biocompatible fastener can include at least one natural polymer that can be derived from a natural source. Natural polymers can include polysaccharides, proteins, and the like. Examples of some suitable polysaccharides include methylhydroxyethylcellulose, hydroxymethylethylcellulose, carboxymethylcellulose, methylcellulose, ethylcellulose, hydroxyethylcellulose, hydroxyethylpropylcellulose, amylopectin, amylose, seagel, starches, starch acetates, starch hydroxyethyl ethers, ionic starches, longchain alkylstarches, dextrins, amine starches, phosphate starches, and dialdehyde starches, alginic acid, phycocolloids, agar, gum arabic, guar gum, locust bean gum, gum karaya, gum tragacanth, and the like. Examples of some proteinaceous materials include, but are not limited to, collagens, caseins, and the like. Moreover, these natural polymers can also impart biodegradable characteristics to the fastener.

In one embodiment, the biodegradable polymers can be reinforced with fibers comprised of magnesium, wherein such fibers can significantly strengthen the fasteners. For example, short fibers, which are added to the polymer during the injection molding process, can be oriented in the direction of the flow so as to significantly improve the mechanical properties, such as strength. Additionally, the magnesium fibers can be pretreated with corona plasma or other well-known method to improve the interface between the polymers and fiber. Since pure magnesium can be highly reactive with water or body fluids, the polymer matrix can act as a shield and protect against fast degradation and magnesium reactions. It can also be understood that optionally the fastener can be formed completely from magnesium and subsequently coated with a polymer coating to shield and protect against fast degradation.

In one embodiment, short fibers of biodegradable micro or nano-porous silicon materials, biodegradable ceramics, organic materials can be added to the polymer. The short fibers, which are added to the polymer during the injection molding process, can be oriented in the direction of the flow and significantly improve the mechanical properties, such as strength, of the resulting fastener. Optionally, these degradable fibers can be pretreated with corona plasma or other well-known method to improve the interface between the polymer matrix and the fiber. Also, the rate of fiber biodegradation can be slowed by being encapsulated within the polymer matrix.

The addition of fibers into the implantable fastener can improve many of the mechanical or strength characteristics of the implantable fastener. In part, this can arise from the nature of the fibers, and/or being oriented with the polymer molecules. For example, the fibers can increase the Young's modulus, increase the strength, and decrease the shrinkage.

In one embodiment, the biodegradable polymers, inert polymers, natural polymers, magnesium fibers, and/or porous silicon fibers can be prepared into a polymeric blend that is comprised of different types of polymers and materials. As such, a polymeric blend can be configured to achieve injection moldability, polymer molecule orientation, and high initial strength. Moreover, the biodegradable polymers and/or natural polymers can be blended in order to achieve biodegradable fasteners that can degrade over time after being implanted.

In another embodiment, the fastener can be fabricated from biodegradable micro or nano-porous silicon materials, biodegradable ceramics, or organic materials. Optionally, the pate made from one or more of these materials and ceramics can be coated or covered with a polymer or polymer matrix.

The present invention overcomes the problems with the existing technology by providing a fastener that allows a secure transmission of torque into the fastener without the risk of damaging the fastener head. The present invention also solves the problems with securely mounting non-metallic fasteners to a driver to maintain the fastener sterilization. In addition, the fastener of the present invention can guide particles or material dislodged from the bone or structure into which the fastener is driven to limit binding of the fastener during positioning of the fastener within the bone or structure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical fastener comprising:
   a head portion comprising a recessed inner surface having a first cylindrical portion that includes a plurality of indentations and plurality of extensions, each of said plurality of indentations and extensions extending across the first cylindrical portion, a second tapered portion having a first angle tapering substantially inward and away from the first cylindrical portion and toward a third portion that extends from the second tapered portion, the second tapered portion including a plurality of indentations and plurality of extensions, each of said plurality of indentations and extensions extending across the second tapered portion, the third portion having a generally cylindrical, substantially uniform cross-sectional profile, and a generally rounded base;
   the plurality of indentations and extensions disposed on the recessed inner surface cooperatively forming a driver contact surface area, said driver contact surface area extending across the first cylindrical portion and the second tapered portion to the third portion; and
   a threaded body portion having threads formed on at least a portion thereof, the threaded body portion extending from the head portion, wherein the threaded body portion comprises a first end located adjacent to the head portion such that the third portion of the recessed inner surface extends into the first end of the threaded body portion so as to extend to an interior of the threaded body portion, a second end located distal to the first end, and a channel extending from the second end toward the first end, the channel having an open end at the second end, the channel being positioned to collect particles from a hole receiving the threaded body portion, the channel traversing a plurality of the threads in the threaded body portion.

2. The medical fastener as recited in claim 1, the plurality of indentations and the plurality of extensions of each of the first cylindrical portion and the second tapered portion having a generally star-shaped cross-section.

3. The medical fastener as recited in claim 1, wherein each of the head portion and the threaded body portion are made from a material selected from the group consisting of a polymeric material, a biodegradable material, or a ceramic material.

4. The medical fastener as recited in claim 3, wherein the polymeric or biodegradable material is reinforced by inclusion of a fibrous material comprised of biodegradable magnesium, biodegradable silicon, or biodegradable ceramic.

5. The medical fastener recited in claim 1, wherein each of the first cylindrical portion, the second tapered portion, the third portion, and the threaded body portion are coated with a polymer coating.

6. A medical screw comprising:
   a head portion comprising a recess having a first portion that includes a plurality of indentations and plurality of extensions, each of said plurality of indentations and extensions extending across the first portion, a second tapered portion tapering substantially inward and away from the first portion and toward a third cylindrical portion extending from the second tapered portion, the second tapered portion including a plurality of indentations and plurality of extensions, each of said plurality of indentations and extensions extending across the second tapered portion, the third cylindrical portion having a generally cylindrical, substantially uniform cross-sectional profile, and a generally rounded base;

the plurality of indentations and extensions disposed on the recess cooperatively forming a driver contact surface area, said driver contact surface area extending across the first portion and the second tapered portion to the third portion; and a threaded body portion having at least one thread that winds around a portion of the threaded body portion in a first direction, the threaded body portion extending from the head portion, the threaded body portion comprising a first end located adjacent to the head portion such that the third cylindrical portion of the recess extends into the first end of the threaded body portion, a second end located distal to the first end, and a channel extending from the second end toward the first end in a second direction opposite to the first direction, the channel having an open end at the second end, the channel traversing at least a portion of the at least one thread, wherein the head portion and the threaded body portion are made from a biodegradable material, wherein each of the first portion, the second tapered portion, the third cylindrical portion, and the threaded body portion are coated with a polymer coating.

7. The medical screw as recited in claim 6, the plurality of indentations and the plurality of extensions of each of the first portion and the second tapered portion having a generally star-shaped cross-section.

8. The medical screw as recited in claim 7, wherein the first portion and the second tapered portion receive a driver having a Torx geometry.

9. The medical screw as recited in claim 6, wherein the biodegradable material is reinforced by inclusion of a fibrous material comprised of biodegradable magnesium, biodegradable silicon, or biodegradable ceramic.

10. The medical screw as recited in claim 6, wherein a driver comprising a pin interference fits within the third portion.

11. A system for mounting a medical fastener to a bone of a patient, the system comprising:

a driver of a first material comprising a tip having a first portion, a second tapered portion, and a pin having a substantially uniform cross-sectional profile extending from the second tapered portion, the first portion and the second tapered portion having a plurality of indentations and extensions disposed thereon that cooperatively form a fastener contact surface area extending across the first portion and second tapered portion to the pin of the driver; and a medical fastener of a second material comprising a head portion and a threaded body portion, the head portion having a recessed inner surface that receives the tip of the driver, the recessed inner surface comprising a first portion that includes a plurality of indentations and plurality of extensions, each of said plurality of indentations and extensions extending across the first portion, a second tapered portion tapering substantially inward and away from the first portion and toward a third cylindrical portion extending from the second tapered portion into the threaded body portion, the second tapered portion including a plurality of indentations and plurality of extensions, each of said plurality of indentations and extensions extending across the second tapered portion, the third cylindrical portion adapted to receive the pin, the third cylindrical portion having a substantially uniform cross-sectional profile that is smaller than the cross-sectional profile of the pin when separate, said first portion and second tapered portion of the recessed inner surface cooperatively forming a driver contact surface area extending across the first portion and second tapered portion to the third cylindrical portion of the recessed inner surface, wherein each of the first portion, the second tapered portion, and the third cylindrical portion of the recessed inner surface are configured to contact and engage with the first portion, the second tapered portion, and the pin of the driver to facilitate driving of the medical fastener by the driver, and wherein the first material is harder than the second material such that the pin of the driver deforms the third cylindrical portion of the recessed inner surface when disposed therein.

12. The system as recited in claim 11, wherein the pin is disposed in the third cylindrical portion of the recessed inner surface such that the driver is coupled to the medical fastener.

13. The system as recited in claim 12, wherein the pin interference fits with the third cylindrical portion of the recessed inner surface.

14. The system as recited in claim 12, wherein at least a portion of the pin has a roughened surface.

15. The system as recited in claim 12, wherein one or more portions of the tip interference fits with at least one of the first portion and the second portion of the medical fastener.

16. The system as recited in claim 11, wherein the medical fastener has a Young's Modulus that is lower than that of the driver.

17. The system as recited in claim 11, wherein the threaded body portion comprises a first end located adjacent to the head portion, a second end located distal to the first end, and a channel extending from the second end toward the first end the channel being positioned to collect particles from a hole receiving the threaded body portion.

18. The system as recited in claim 17, wherein the channel comprises an open end at the second end of the threaded body portion.

19. The system recited in claim 11, wherein each of the first portion, the second tapered portion, the third cylindrical portion, and the threaded body portion of the medical fastener are coated with a polymer coating.

* * * * *